United States Patent

Kreckel

[11] 4,051,348
[45] Sept. 27, 1977

[54] CONTACT LENS DISINFECTING CIRCUIT
[75] Inventor: Kurt H. Kreckel, Fairport, N.Y.
[73] Assignee: Bausch & Lomb Incorporated, Rochester, N.Y.
[21] Appl. No.: 597,124
[22] Filed: July 18, 1975
[51] Int. Cl.² .............................................. H05B 1/02
[52] U.S. Cl. ................................. 219/506; 219/492
[58] Field of Search ............... 219/109, 248, 453, 485, 219/506, 412, 413, 443, 446, 240, 327, 334, 492; 236/94; 337/376, 79; 340/227 R, 227.1, 228 R; 317/40 R, 41

[56] References Cited
U.S. PATENT DOCUMENTS

| 3,612,826 | 10/1971 | Deaton | 219/453 |
| 3,621,202 | 11/1971 | Gemert | 219/492 |

*Primary Examiner*—J. V. Truhe
*Assistant Examiner*—Fred E. Bell
*Attorney, Agent, or Firm*—Frank C. Parker; Bernard D. Bogdon

[57] ABSTRACT

An electrical circuit for use in a contact lens care unit for disinfecting lenses includes two thermostats one of which is manually set to electrically energize a heating device for disinfecting lenses and an indicator element for providing visible representation of the operational state of the unit. The second of which thermostats automatically energizes to provide a parallel electrical energizing path to the indicator for a period of time after the first thermostat automatically deenergizes the heating device. The indicator is thereby continually energized throughout a complete contact lens care cycle to provide prominent representation of the operational state of the unit.

10 Claims, 2 Drawing Figures

CONTACT LENS DISINFECTING CIRCUIT

BACKGROUND OF THE INVENTION

1. Field of the Invention

The purpose of this invention is to provide an improved electrical circuit for use in disinfecting contact lenses and more particularly an electrical circuit for use in providing dry heat primarily for heat transfer by conduction to a contact lens carrying case to disinfect the contact lenses carried therein.

2. Description of the Prior Art it is appreciated that the application of heat is an ideal way to disinfect contact lenses particularly those having hydrophilic properties and characteristics. The most satisfactory practice has been to disinfect contact lenses through the use of devices which heat fluids, particularly water, to a state of vaporization. By means of convection the vaporization and steam generated, heat the exterior of a contact lens carrying case to bring and maintain the temperature of the interior of the case and the fluids and lenses within the case at a disinfecting temperature for a minimum period of time.

One device of this nature is described in the disclosure of U.S. Pat. No. 3,585,362, entitled PORTABLE ELECTRICAL HEATING DEVICE, for inventors Paul A. Hoogesteger and Charles R. McDougal, issued June 15, 1971. These types of prior art devices require the presence and use of a fluid, principally water, and are frequently inconvenient to use and generally require that special care be exercised in their use and that the unit be regularly wiped dry and cleaned before and after use.

SUMMARY OF THE INVENTION

This invention provides an electrical circuit exceptionally suitable for use in disinfecting contact lenses. One which overcomes the inconveniences of prior art devices and provides for an indicating device to identify throughout the operation, the state of the disinfecting cycle in order to insure completion of the cycle and provide safety of operation to the user.

A full operational cycle for the care of hydrophilic contact lenses within a disinfecting unit basically consists of a heat build-up period, a disinfecting period for destroying pathogenic microorganisms and a cool-down period. For the preferred embodiment, the disinfecting period commences before the completion of the heat build-up period and terminates after the start of the cool-down period.

The heating device is energized by the user manually setting a switch to complete an electrical circuit and provide electrical current to a heater and to commence the heat build-up period. Simultaneously with the energization of the heater, an indicator device is energized to provide a visible indication to the operator that the unit is operating and that the heater is turned on and in a heating mode. As the temperature of the heating device increases and before it reaches a desired maximum, a second switch is automatically closed to insure that the indicator device operates throughout the complete lens care cycle. Although somewhat arbitrary, at about the time the second switch closes, the disinfecting period commences. When the heater reaches the maximum selected temperature, the first switch automatically opens to break the electrical circuit and deenergize the heater. A predetermined level of temperature is maintained within the disinfecting unit for a sufficient period of time to disinfect the contact lenses.

During the lens care cycle the indicator device continually provides an indication that the unit is in operation. At a temperature far below the disinfecting temperature, the second switch automatically opens and the indicator device is turned off, the cool-down period terminates and the cycle is complete. The system is then ready for a repeat operation when necessary for the care of the contact lenses.

DETAILED DESCRIPTION OF THE PREFERRED EMBODIMENT

This patent specification is cross referenced to patent specifications and disclosures of concurrently filed and copending U.S. Patent Applications entitled Apparatus and Process for Disinfection of Hydrophilic Contact Lenses, Ser. No. 597,125 for inventors J. Kadlecik and W. Manning; Design For Contact Lens Disinfection Apparatus, Ser. No. 597,126 for inventor P. Hoogesteger and Switching Means for Contact Lens Disinfecting Apparatus, Ser. No. 597,127, now U.S. Pat. No. 3,983,362, Sept. 28, 1976 for inventors P. Hoogesteger and J. Kadlecik. In the first of the beforementioned cross referenced patent applications is a description of an inventive preferred embodiment for a contact lens disinfecting unit. That description is inclusive of the physical aspects of the disinfecting unit and the thermal aspects of disinfecting contact lenses. The preferred embodiment described herein will set forth principles of an invention which is ideally suited for use in combination with the inventions of the beforementioned patent applications.

In a disinfecting process, which is sometimes referred to as an aseptizing process for contact lenses having hydrophilic properties and characteristics, it is appreciated that the temperature of the lenses must be raised to a specific temperature and maintained at or about that temperature for a minimum period of time.

Figure 1:
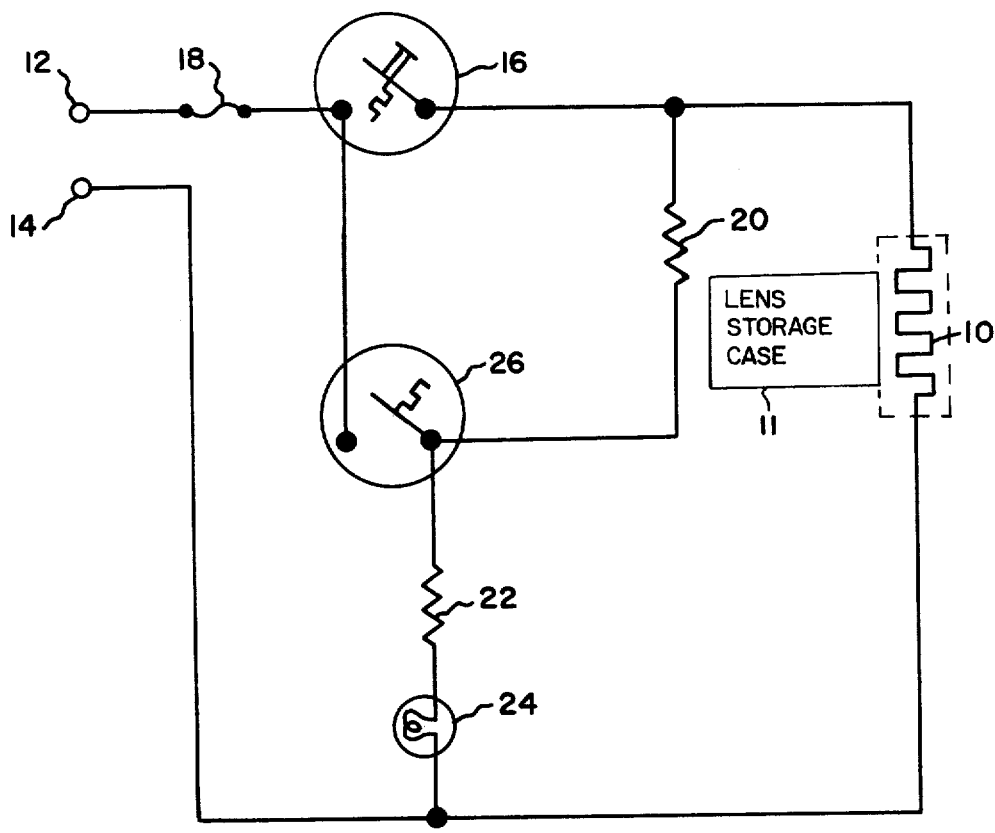
FIG. 1 is a schematic illustration of an electrical circuit for use in the care of contact lenses according to the principles of the invention.

In FIG. 1 there is schematically illustrated an electrical disinfecting circuit and specifically an electrical heater element 10 for providing the heat to raise the temperature of the contact lenses to be disinfected and carried within a lens storage case 11. Since contact lenses are opthalmic vision aids which normally require daily care such as being disinfected, the lens care unit is one which is generally used in a household environment. In such an environment the electrical energy necessary to cause the electrical heater element 10 to heat is available at standard household electrical receptacles. Electrical connection is made to such household receptacles through the use of any standard and convenient means such as an electrical cord. In is appreciated that the cord may be permanently connected to the internal electrical circuit of the care unit or, as a matter of design choice or convenience, be detachable from the unit. The schematically illustrated electrical circuit of FIG. 1 provides for connection to the electrical energy source at terminals 12 and 14.

Further, the circuit attachment to the electrical source and the other circuit elements are adaptable to energize the heater regardless of the frequency, voltage level or type of electrical energy available at the source. It will be appreciated that requirements of electrical codes or standards, such as separate electrical grounding, can easily be accommodated.

The heater 10 is electrically energized when a thermostatic switch 16 has been closed by manual actuation, as set forth, for example, in the beforementioned Apparatus and Process for Disinfection of Hydrophilic Contact Lenses patent application. When the thermostatic switch 16 completes the electrical circuit, alternaitng current from the source connected to terminals 12 and 14 provides electrical energy to serially connected thermal fuse 18 and parallel electrical paths for the heater and indicator. One leg of the parallel path includes the heater 10 and the other leg of the parallel path includes first and second current limiting resistors 20 and 22 and a lamp indicator 24 in direct electrical contact with circuit terminal 14.

Figure 2:
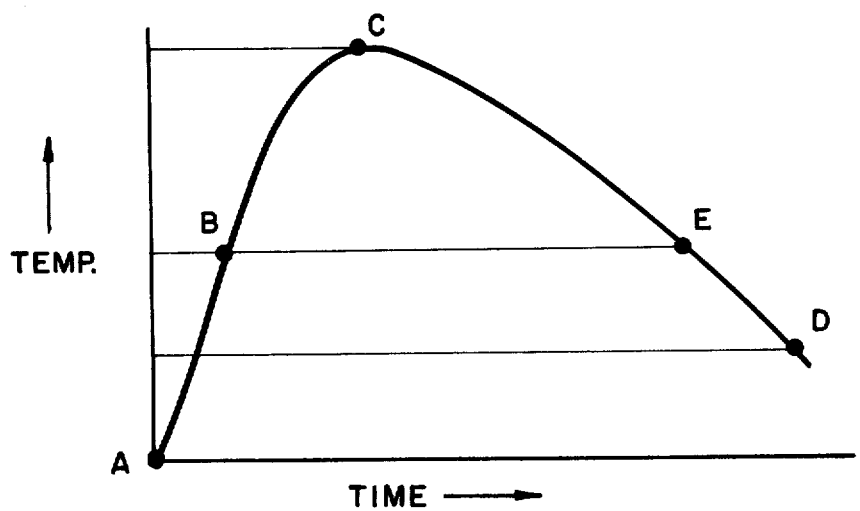
FIG. 2 is an illustration of a time/temperature graph identifying the time and temperature points for operation of the switches, indicator and heater of the electrical circuit of FIG. 1.

FIG. 2 illustrates, by means of a time-temperature graphical curve, the heat build-up within the heater 10 and identifies points along the curve, which describe the status of operation of the circuit elements on a time-temperature basis. Specifically, Point A indicates when the thermostat 16 is manually set, the heater 10 is electrically energized and the lamp indicator 24 is illuminated.

Responsive to the temperature build-up of the heater 10 is an automatic thermostat 26 which energizes only after its thermal element reaches a specific temperature identified by somewhat arbitrarily located Point B on the graph of FIG. 2. When the thermostat 26 automatically closes, it provides a less electrically resistant path for the current and current limiting resistor 20 is effectively bypassed. Even when thermostat 26 is closed, it will be appreciated that electrical current is still energizing heater 10 and the temperature of heater 10 will continue to increase. At some predetermined temperature the thermal element of the manually set thermostat 16 will automatically break the electrical circuit to thereby electrically disengage the heater 10 and discontinue its heating operation. Point C of FIG. 2 illustrates, relatively, the time and temperature point at which the heater 10 is shut off. It will be appreciated that after that time the heater 10 will slowly dissipate its thermal energy into and through the body of the lens care unit and slowly into the atmosphere.

The heater and thermostatic switches cool down at a time-temperature rate typical of that described by the curve of the graph in FIG. 2 from Point C to Point D. After sufficent cooling down has transpired and the thermal element of thermostat 26 has reached a sufficiently low predetermined temperature, thermostat 26 will automatically open thereby opening the electrical current path to the indicator lamp 24 and the lamp will no longer be illuminated. The lens care unit has then completed a full operational cycle over a controlled period of time, having gone from an ambient room temperature at Point A, to a minimum disinfecting temperature at approximately Point B, to and through a maximum heater temperature at Point C and finally down to a temperature slightly above normal ambient at Point D where the unit is turned off.

It will be appreciated that the time period represented by the time duration from Point B to Point E is at least the minimum time for disinfecting contact lenses at the minimum temperature identified by the temperature level of Point B and E. Further, it will be appreciated that the lens care unit temperature cool down occurs over a time period identified by the time from Point C to Point D and specifically that the time from Point E to Point D is a cool-down time period to insure that the contact lens carrying case has reached a comfortable touching temperature identified at the temperature level of Point D.

It will be further appreciated that the absolute temperatures of Point C and D are somewhat arbitrary and are considered and generally selected in conformance with available products and design standards. In addition, it will be appreciated that Pint B could possibly be located anywhere betwen Points A and C along the graph curve of FIG. 2. After thermostat 26 is closed the slope of the temperature curve between Points B and C of FIG. 2 is lessened. It is of course necessary that the disinfecting circuit insure that the contact lenses within the carrying case are maintained at at least a minimum temperature for a minimum period of time to disinfect. The thermal fuse 18 is provided as a safeguard to prevent damage to the contact lenses and the lens care unit.

Although not particularly critical to the typical schematic design of the inventive electrical thermal circuit embodiment of FIG. 1, it will be appreciated that the following exemplary thermal values are instrumental in selecting the type, rating and accuracy values of the electrical components of the circuit. The minimum disinfecting temperature is approximately 80° C maintained for a minimum period of approximately 10 minutes and the thermostate 16 is designed to shut off the heater at approximately 120° C. Complete shut down of the system is provided for at approximately 52° C as identified by Point D of FIG. 2. The thermal fuse 18 will automatically break the electrical circuit if, for example, a temperature of 150° C is reached. It will be appreciated that the electrical elements schematically illustrated in FIG. 1 can either be electrically connected by typical electrical wire which is circular in diameter or flat electrical wire or, for example, some can be incorporated on a printed circuit board assembly for convenience of manufacturing and servicing.

The circuit elements can typically be elements readily available. The heater may have a capacity of approximately 25 watts and a heat density of about 9.5 watts per square inch. It is generally desirable to insulate the heater 10 with any suitable insulation material such as silicone rubber and fiber glass material. The manual reset thermostat 16 is selected to have an open temperture at approximately 120° C and has an 8 ampere rating. The automatic thermostat 26 closes at approximately 80° C and opens when the temperature is reduced to approximately 50° C and also has an 8 ampere rating. The lamp 24 for the convenience of assembling into the schematic circuit of FIG. 1 can have incorporated with it, the current limiting resistor 22.

It is claimed:

1. A contact lens disinfecting electrical control circuit for use in thermally disinfecting lenses by elevating the temperture of the contact lenses for a predetermined period of time, comprising:

heating means responsive to electrical energy for providing heat to a contact lens storage device and elevating the temperature of the contact lenses to disinfect the lenses;

indicator means for providing a readily detectable indication that during operation of the heating means the temperature of the contact lenses is elevated above ambient temperature;

first control means including switching contacts for manual operation of the switching contacts to connect the heating means to an electrical source and for automatic operation of the switching contacts responsive to the heat provided to the contact lens storage device by the heating means to disconnect the heating means from the energy source; and second control means for automatic operation responsive to the heat provided to the contact lens storage device by the heating means to energize the indicator means for a period of time after the heating means has been disconnected from the energy source.

2. The electrical control circuit as defined in claim 1, wherein the switching contacts of the first control means for manual operation, in addition to connecting the heating means to the electrical energy source, simultaneously energizes the indicator means for the indicator means to provide indication that the temperature of the contact lenses is being elevated above ambient temperature.

3. An electrical control circuit for use in thermally disinfecting contact lenses by elevating the temperature of the contact lenses for a predetermined period of time, comprising:

heating means responsive to electrical energy for providing heat to a contact lens storage device and elevating the temperature of the contact lenses to disinfect the lenses;

heater control means including switching contacts for manual operation of the switching contacts to connect the heating means to an electrical energy source and for automatic operation of the switching contacts responsive to the heat provided to the contact lens storage device by the heating means to disconnect the heating means from the energy source; and indicator means for providing a readily detectable indication, as a function of the elevating temperature, that the temperature of the contact lenses is being elevated above ambient temperture, further including indicator control means separate from the heater control means for automatic operation responsive to the heat provided to the contact lens storage device by the heating means to provide that the indicator means provides detectable indication of the elevated temperature for at least a period of time after the heating means has been disconnected from the energy source.

4. A contact lens disinfecting electrical thermal control circuit, comprising:

a heater element responsive to an electrical current for providing heat to a contact lens storage device;

a first control means for manual activation to complete an electrical circuit from an electrical energy source to the heater element, which control means is heat sensitive at a first predetermined temperature to disconnect the heater element from the electrical energy source;

second control means automatically operative at a second predetermined temperature to complete an electrical circuit in parallel with the heater element and automatically disconnect the circuit in parallel at a predetermined temperature lower than the second predetermined temperature; and indicator means for providing an indication when either the first or the second control means completes an electrical circuit.

5. The contact lens disinfecting control circuit as defined in claim 4, wherein the first control means is a manual reset thermostat.

6. The contact lens disinfecting control circuit as defined in claim 4, wherein the second control means is an automatic thermally controlled thermostat.

7. The contact lens disinfecting control circuit as defined in claim 4, wherein the first control means is a manual reset thermostat and the second control means is an automatic thermally controlled thermostat.

8. The contact lens disinfecting control circuit as defined in claim 4, wherein the indicator means provides a visual indication when either the first or the second control means completes an electrical circuit.

9. The contact lens disinfecting control circuit as defined in claim 8, wherein the indicator means providing the visual indication is illuminated.

10. The contact lens disinfecting control circuit as defined in claim 9, wherein the indicator means providing the illuminated visual indication is a lamp.

* * * * *